United States Patent
Hashimoto et al.

(10) Patent No.: US 9,226,728 B2
(45) Date of Patent: Jan. 5, 2016

(54) ULTRASONIC DIAGNOSTIC APPARATUS AND CONTROL METHOD THEREOF

(75) Inventors: Shinichi Hashimoto, Otawara (JP);
Tetsuya Kawagishi, Kasushiobara (JP);
Takuya Sasaki, Nasu-gun (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 1098 days.

(21) Appl. No.: 12/106,625

(22) Filed: Apr. 21, 2008

(65) Prior Publication Data
US 2008/0262348 A1 Oct. 23, 2008

(30) Foreign Application Priority Data
Apr. 23, 2007 (JP) ................... 2007-113336

(51) Int. Cl.
| A61B 8/08 | (2006.01) |
| A61B 8/14 | (2006.01) |
| A61B 8/00 | (2006.01) |
| G01S 7/52 | (2006.01) |
| G01S 15/89 | (2006.01) |

(52) U.S. Cl.
CPC ... *A61B 8/08* (2013.01); *A61B 8/14* (2013.01); *A61B 8/145* (2013.01); *A61B 8/463* (2013.01); *A61B 8/465* (2013.01); *A61B 8/483* (2013.01); *A61B 8/523* (2013.01); *G01S 7/52052* (2013.01); *G01S 7/52074* (2013.01); *G01S 7/52084* (2013.01); *A61B 8/0883* (2013.01); *A61B 8/543* (2013.01); *G01S 15/8993* (2013.01)

(58) Field of Classification Search
CPC .......... A61B 8/08; A61B 8/0883; A61B 8/14; A61B 8/145; A61B 8/463; A61B 8/465; A61B 8/483; A61B 8/523; A61B 8/543; G01S 15/8993; G01S 7/52052; G01S 7/52074; G01S 7/52084
USPC .................................. 600/437, 443; 382/128
See application file for complete search history.

(56) References Cited

U.S. PATENT DOCUMENTS

| 6,106,467 A * | 8/2000 | Shimizu ................... 600/443 |
| 6,245,017 B1 * | 6/2001 | Hashimoto et al. ....... 600/447 |
| 6,544,175 B1 | 4/2003 | Newman |
| 7,314,446 B2 * | 1/2008 | Byrd et al. ............... 600/443 |
| 7,881,774 B2 * | 2/2011 | Kobayashi ............... 600/428 |
| 7,951,082 B2 * | 5/2011 | Kawabata et al. ......... 600/437 |
| 2005/0187474 A1 * | 8/2005 | Kwon ...................... 600/437 |

FOREIGN PATENT DOCUMENTS

| CN | 1636521 A | 7/2005 |
| EP | 1 685 799 A1 | 8/2006 |

(Continued)

OTHER PUBLICATIONS

Office Action issued Sep. 11, 2012 in Japanese Patent Application No. 2008-074512 (with English-language translation).

*Primary Examiner* — Katherine Fernandez
(74) *Attorney, Agent, or Firm* — Oblon, McClelland, Maier & Neustadt, L.L.P.

(57) ABSTRACT

An ultrasonic diagnostic apparatus generates volume data by performing three-dimensional scan of a three-dimensional region with an ultrasonic wave. An input unit sets or changes at least one of a plurality of correlated scan conditions for the three-dimensional scan. A determination unit determines the other scan conditions of the plurality of scan conditions on the basis of at least one scan condition that is set or changed. A display unit displays at least one of the set or changed scan condition and the determined scan conditions.

13 Claims, 8 Drawing Sheets

(56) References Cited

FOREIGN PATENT DOCUMENTS

| JP | 11-221217 A | 8/1999 |
| JP | 2000-135217 A | 5/2000 |
| JP | 2006-400 A | 1/2006 |
| JP | 2006-501920 A | 1/2006 |
| JP | 2006-254985 A | 9/2006 |
| JP | 2007-21018 A | 2/2007 |

* cited by examiner

ULTRASONIC DIAGNOSTIC APPARATUS AND CONTROL METHOD THEREOF

CROSS-REFERENCE TO RELATED APPLICATIONS

This application is based upon and claims the benefit of priority from prior Japanese Patent Application No. 2007-113336, filed Apr. 23, 2007, the entire contents of which are incorporated herein by reference.

BACKGROUND OF THE INVENTION

1. Field of the Invention

The present invention relates to an ultrasonic diagnostic apparatus that makes a diagnosis by imaging the inside of a body using an ultrasonic wave and a control method thereof and in particular, to an ultrasonic diagnostic apparatus that displays an ultrasonic image in a three-dimensional manner and a control method thereof.

2. Description of the Related Art

In recent years, the ultrasonic diagnostic apparatus may collect and display an image using three-dimensional scan. In addition, a diagnosis using a three-dimensional real-time imaging method of scanning a three-dimensional region (for example, a region including the heart) inside a tested body while displaying a two-dimensional or three-dimensional image of the region in real time is also widespread.

A technique of generating volume data on a desired range by connecting volume (sub volume) data on a small region collected in response to a predetermined matched trigger (for example, in synchronization with ECG) on the basis of the matched trigger and of maintaining a real-time property by sequentially updating sub volume data according to time information is also developed in order to secure a wider volume scan region (scan region of a three-dimensional region) in the three-dimensional real-time imaging method (hereinafter, this technique is referred to as a 'three-dimensional trigger scan mode').

In addition, a known document related to this application includes U.S. Pat. No. 6,544,175, for example.

In the case of performing image collection by a three-dimensional trigger scan mode, there is a problem that a work load of a user is large. In the case of observing the heart in the three-dimensional trigger scan mode, it is general to display an ultrasonic image corresponding to three sections of Basal/Mid/Apical corresponding to ASE division. In the known ultrasonic diagnostic apparatus, however, alignment of the three sections of Basal/Mid/Apical, adjustment of a scan range (that is, an angle of view) for optimizing a volume rate, and the like should be performed while observing an image actually obtained by the three-dimensional trigger scan mode. As a result, since a work load at the time of photographing is increased, a user's burden is increased. In addition, if image collection is not performed well and a photographing time is increased, a burden is given to a patient as well as a user.

SUMMARY OF THE INVENTION

The invention has been finalized in view of the above situation, and it is an object of the invention to provide an ultrasonic diagnostic apparatus and a control method thereof that can alleviate the work load of a user in a case of performing image collection by the three-dimensional scan mode compared with those in the related art.

According to a first aspect of the invention, an ultrasonic diagnostic apparatus that generates volume data by performing three-dimensional scan of a three-dimensional region with an ultrasonic wave includes: an input unit that sets or changes at least one of a plurality of correlated scan conditions for the three-dimensional scan; a determination unit that determines the other scan conditions of the plurality of scan conditions on the basis of at least one scan condition that is set or changed; and a display unit that displays at least one of the set or changed scan condition and the determined scan conditions.

According to a second aspect of the invention, an ultrasonic diagnostic apparatus that generates volume data by performing three-dimensional scan of a three-dimensional region with an ultrasonic wave includes: an image acquisition unit that acquires a prescan image regarding at least one section crossing the three-dimensional region by executing prescan in a stage before the three-dimensional scan; a section setting unit that sets at least one section on the prescan image; and a display unit that displays the position of at least one set section on the prescan image.

According to a third aspect of the invention, a control method of an ultrasonic diagnostic apparatus that generates volume data by performing three-dimensional scan of a three-dimensional region with an ultrasonic wave includes: setting or changing at least one of a plurality of correlated scan conditions for the three-dimensional scan; determining the other scan conditions of the plurality of scan conditions on the basis of at least one scan condition that is set or changed; and displaying at least one of the set or changed scan condition and the determined scan conditions.

According to a fourth aspect of the invention, a control method of an ultrasonic diagnostic apparatus that generates volume data by performing three-dimensional scan of a three-dimensional region with an ultrasonic wave includes: acquiring a prescan image regarding at least one section crossing the three-dimensional region by executing prescan in a stage before the three-dimensional scan; setting at least one section on the prescan image; and displaying the position of at least one set section on the prescan image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DESCRIPTION OF THE PREFERRED EMBODIMENTS

Hereinafter, an ultrasonic diagnostic apparatus and a control method thereof according to embodiments of the invention will be described with reference to the accompanying drawings.

Figure 1:
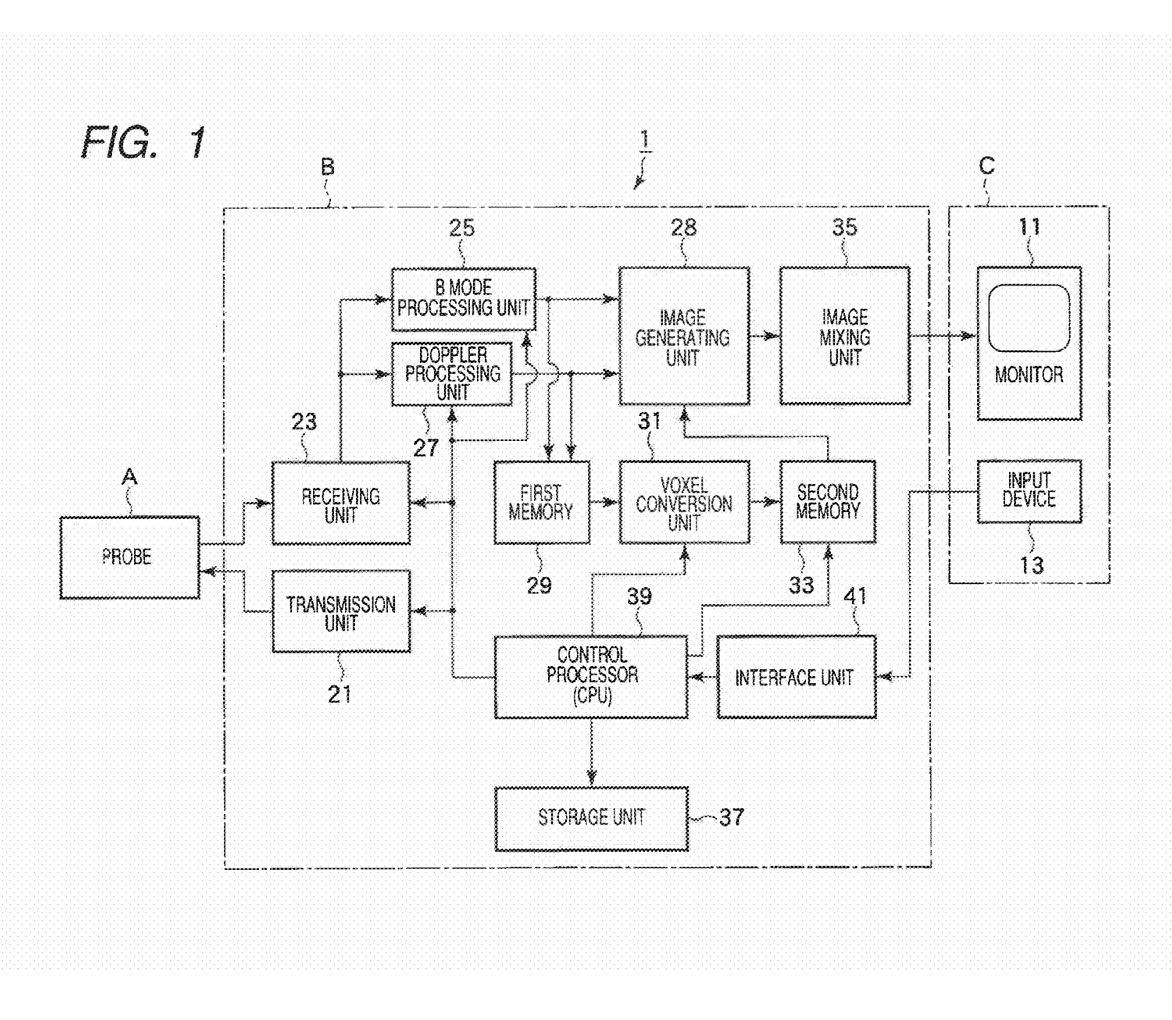
FIG. 1 is a block diagram illustrating the configuration of an ultrasonic diagnostic apparatus according to an embodiment of the invention.

FIG. 1 is a block diagram illustrating the configuration of an ultrasonic diagnostic apparatus 1 according to the present embodiment. As shown in FIG. 1, the ultrasonic diagnostic apparatus 1 includes a probe A, an apparatus body B, and an interface portion C.

The probe A generates an ultrasonic wave on the basis of a driving signal from the apparatus body B and has a plurality of vibrators that converts a reflected wave from a tested body into an electric signal, a matching layer attached to the vibrators, a packing material that prevents the ultrasonic wave from being transmitted rearward from the vibrators, and the like. When ultrasonic waves are transmitted from the probe A to the tested body P, the transmitted ultrasonic waves are sequentially reflected on a discontinuous surface of an acoustic impedance of body tissues. The reflected ultrasonic waves are received as echo signals by the probe A. The amplitude of the echo signal depends on a difference between acoustic impedances of two kinds of body tissues with the reflected discontinuous surface as a border. In addition, an echo signal when transmitted ultrasonic waves are reflected from a moving blood flow, a heart wall, and the like is frequency shifted by the Doppler effect.

In addition, in order to make ultrasonic scan of a three-dimensional region of a tested body possible, the probe A has a configuration for performing ultrasonic scan of the three-dimensional region while mechanically swinging vibrators in the direction perpendicular to a direction in which the vibrators are arrayed or a configuration for performing ultrasonic scan of the three-dimensional region by an electric control using vibrators arrayed in a two-dimensional manner. In the case of adopting the former configuration, three-dimensional scan is performed by a swing circuit. Therefore, a checker can automatically acquire a plurality of two-dimensional tomographic images only by bringing the probe A into contact with a tested body. Since a swinging speed is controlled, an exact distance between sections can be detected. In the case of adopting the latter configuration, in principle, ultrasonic scan based on electronic three-dimensional scan can be performed by delay processing on an electric signal in the same manner as two-dimensional scan.

The interface portion C includes a monitor 11 and an input device 13.

The monitor 11 displays morphological information (B-mode image) in the body, blood flow information (including an average speed image, a distributed image, and a power image), and a combination thereof as an image on the basis of a video signal from the apparatus body B.

In addition, the monitor 11 displays various kinds of scan conditions, the position of an arbitrary section, and a model expressing a scan range in processing (processing for supporting three-dimensional trigger scan) based on a function (will be described later) for supporting three-dimensional trigger scan and a screen for setting and changing those described above.

The input device 13 is connected to the apparatus body B and has various switches, buttons, a track ball, a mouse, a keyboard, and the like used to perform various kinds of instructions from an operator, an inspection for setting a condition or a region of interest (ROI), an instruction for setting various image quality conditions, and the like to the apparatus body B. For example, when a user operates an end button or a FREEZE button of the input device 13, transmission and reception of an ultrasonic wave is ended and the ultrasonic diagnostic apparatus is temporarily stopped.

In addition, the input device 13 has switches for setting and changing various kinds of scan conditions, the position or slope of an arbitrary section, and the direction of a model expressing a scan range in processing for supporting the three-dimensional trigger scan.

The apparatus body B includes a transmission unit 21, a receiving unit 23, a B-mode processing unit 25, a Doppler processing unit 27, an image generating unit 28, a first memory 29, a voxel conversion unit 31, a second memory 33, an image mixing unit 35, a storage unit 37, a processor unit (CPU) 39, and an interface unit 41.

The transmission unit 21 has a trigger generating circuit, a delay circuit, and a pulse circuit which are not shown in the drawing. The pulse circuit repeatedly generates a rate pulse for forming a transmitted ultrasonic wave in a predetermined rate frequency fr Hz (period; 1/fr second). The delay circuit makes ultrasonic waves converge in the beam shape for every channel and gives a delay time, which is required to determine the transmission directivity, to each rate pulse. The trigger generating circuit applies a driving pulse to the probe A at a timing based on the rate pulse.

The receiving unit 23 has an amplifying circuit, an A/D converter, and an adder which are not shown in the drawing. The amplifying circuit amplifies an echo signal received through the probe A for every channel. The A/D converter gives a delay time, which is required to determine the receiving directivity, to each amplified echo signal. The adder adds the echo signals to which the delay time is applied. By this addition, a reflected component from a direction according to the receiving directivity of echo signals is emphasized and overall beams in ultrasonic transmission and reception are formed by the receiving directivity and the transmission directivity.

The B-mode processing unit 25 receives an echo signal from the receiving unit 23, performs logarithmic amplification and envelope detection of the received echo signal, and generates data in which the signal strength is expressed as the brightness. This data is transmitted to the image generating unit 28 and is displayed on the monitor 11 as a B-mode image that expresses the strength of a reflected wave as the brightness.

The Doppler processing unit 27 receives the echo signal from the receiving unit 23, analyzes the frequency of the received echo signal, extracts a blood flow or a tissue and a contrast echo component due to the Doppler effect, and calculates blood flow information, such as an average speed, dispersion, and power, with respect to multiple points.

The image generating unit 28 generates an image on the basis of various kinds of data received from the B-mode processing unit 25, the Doppler processing unit 27, and the second memory 33. In addition, data before being input to the image generating unit 28 may be called raw data.

The first memory 29 stores raw data received from the B-mode processing unit 25 or the Doppler processing unit 27.

The voxel conversion unit 31 generates volume data (or sub volume data) corresponding to a predetermined range by using the raw data recorded in the first memory 29.

The second memory 33 stores volume data (or sub volume data) generated in the voxel conversion unit 31. In addition, in response to an instruction from the processor unit 39, the second memory 33 connects a plurality of sub volume data on the basis of predetermined trigger and stores the data as volume data on a desired range. Moreover, in response to the instruction from the processor unit 39, the second memory 33 updates the sub volume data that forms a part of the volume data on a desired range on the basis of time information.

The image mixing unit 35 mixes an image received from the image generating unit 28 with alphabetic information or scales of various parameters, a model indicating a scan condition or a scan range to be described later or an ECG signal image, and the like and outputs the mixing result as a video signal to the monitor 11.

The storage unit 37 is a recording medium, such as a magnetic disk (for example, a floppy (registered trademark) disk or a hard disk), an optical disk (for example, a CD-ROM, a DVD), and a semiconductor memory, and is a device that reads information recorded in the above recording mediums. The storage unit 37 stores a program for realizing a function for supporting transmission and reception conditions, a predetermined scan sequence, and three-dimensional trigger scan, a control program for executing image generation and display processing, a program for creating diagnostic information (for example, a patient ID or doctor's opinion), a diagnostic protocol, a body mark, and other data groups. The data in the storage unit 37 may also be transmitted to an external peripheral device through the interface unit 41.

The processor unit 39 has a function as an information processing device (computer) and controls an operation of the ultrasonic diagnostic apparatus 1. The processor unit 39 reads a program for realizing a function for supporting three-dimensional trigger scan and a control program for executing a predetermined scan sequence and image generation and display from the storage unit 37, loads the read programs onto a memory thereof, and executes an operation, control, and the like regarding various kinds of processing.

The interface unit 41 is an interface related to the input device 13, a network, and a new external storage device (not shown). Data or an analysis result of an ultrasonic image obtained by the apparatus may be transmitted to other apparatuses through the network by the interface unit 41.

(Function of Supporting Three-Dimensional Trigger Scan)

Next, a function for supporting three-dimensional trigger scan that the ultrasonic diagnostic apparatus 1 has will be described. This function can be largely classified into a function for simulating scan conditions, a function for adjusting a sectional position, a function for visualizing a scan range, and a function for simulated three-dimensional scan. Hereinafter, each of the functions will be described. In addition, three-dimensional trigger scan is a scan method of generating volume data on a three-dimensional region by connecting a plurality of sub volume data, which is collected by performing three-dimensional scan of a plurality of sub regions included in the three-dimensional region, on the basis of a predetermined matched trigger in response to the predetermined trigger.

More specifically, in the present embodiment, it is assumed that an object part of image diagnosis is a heart. In addition, more specifically, an arbitrary section set for volume data obtained by three-dimensional trigger scan is a plurality of MPR sections cut from the volume data. For example, the plurality of MPR sections are three C planes (that is, planes not parallel with transmission and reception directions of an ultrasonic wave) of Basal/Mid/Apical corresponding to ASE division. In addition, it is assumed that prescan executed in a stage before a three-dimensional trigger scan mode is a bi-plane scan. However, the technical scope and spirit of the invention are not limited to types of prescan and arbitrary section set for a part to be diagnosed and volume data obtained by three-dimensional trigger scan. For example, an MPR section may be adopted as the arbitrary section set for volume data.

[Function for Simulating Scan Conditions]

The function for simulating scan conditions means that when at least a part of a plurality of correlated scan conditions, which are used in the three-dimensional trigger scan, is input in a stage before the three-dimensional trigger scan mode, the remaining scan conditions are calculated and the input scan conditions and the calculated scan conditions are displayed in a predetermined layout.

In addition, the correlated scan conditions used in the three-dimensional trigger scan include a scan range, a density of scan lines, a frame rate, a gain, a frequency, a dynamic range, filter setting, a viewing field depth, a focus position, a sub volume number, and a volume rate.

Figure 2:
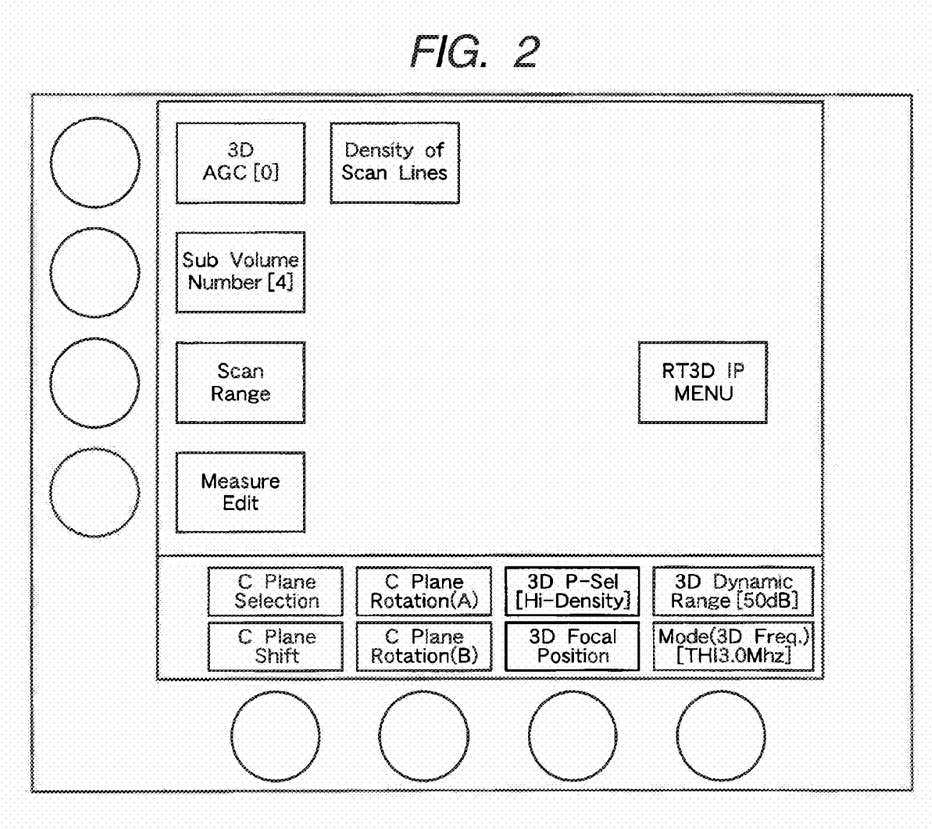
FIG. 2 is a view illustrating an example of a screen for selecting a scan condition, a C plane position, and the like, which are to be set and changed and are displayed on a monitor shown in FIG. 1.

FIG. 2 is a view illustrating an example of a selection screen (user interface) for selecting a scan condition, a C plane position, and the like, which are to be set and changed and are displayed on the monitor 11.

Figure 3:
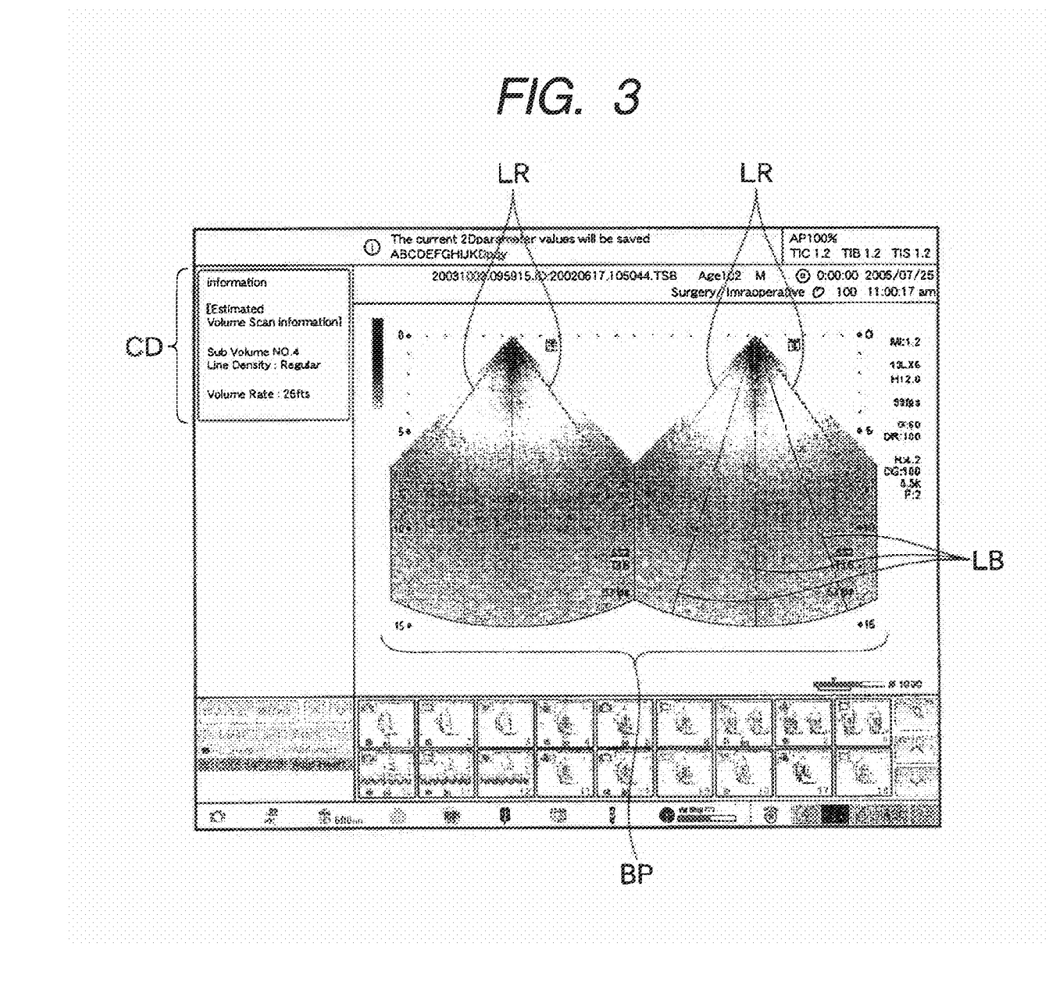
FIG. 3 is a view explaining a function for simulating a scan condition by a processor unit shown in FIG. 1 and illustrates an example of a screen on which a bi-plane image acquired by prescan and a plurality of scan conditions used in three-dimensional trigger scan are displayed.

FIG. 3 is a view explaining a function for simulating a scan condition. FIG. 3 shows an example of a screen of the monitor 11 that displays a bi-plane image BP, which is acquired by prescan, and a plurality of scan conditions CD used in three-dimensional trigger scan.

For example, a scan range (that is, an angle of view) can be set and changed when a 'Scan Range' is selected on the screen shown in FIG. 2. In this state, for example, when an angle of a line LR indicating a three-dimensional scan range shown on (either one of) the bi-plane image BP of FIG. 3 is adjusted by a mouse or an exclusive switch, the processor unit 39 sets or changes a scan range regarding the three-dimensional trigger scan on the basis of the angle of the line LR indicating the three-dimensional scan range after the adjustment.

In addition, for example, the sub volume number can be set and changed when a 'Sub Volume Number' is selected on the screen shown in FIG. 2. In this state, for example, when 'sub volume number 4' is input from the input device 13, the processor unit 39 automatically displays a boundary line LB, which indicates the boundary of sub volume data on the bi-plane image BP, on the monitor 11 as shown in FIG. 3.

In addition, for example, the density of scan lines can be set and changed when 'Density of Scan Lines' is selected on the screen shown in FIG. 2. The processor unit 39 sets or changes the density of scan lines regarding the three-dimensional trigger scan by number input from the input device 13, for example. Various scan conditions that are input are automatically displayed on the monitor 11, for example, in a layout shown in FIG. 3.

In addition, when other scan conditions that can be calculated or determined on the basis of some input scan conditions exist, the processor unit 39 calculates or determines values of the other scan conditions. In other words, as for the function for simulating scan conditions, the processor unit 39 simulates the other scan conditions on the basis of some input scan conditions and displays values, conditions, and the like obtained as a result together with the input scan conditions.

For example, in the case when values of three scan conditions including the scan range, the density of scan lines, and the sub volume number are set or changed as described above, the processor unit 39 calculates a value of a volume rate on the basis of at least the values of the three scan conditions. Typically, the volume rate is calculated on the basis of the scan range, the density of scan lines, the sub volume number, and the viewing field depth. The calculated value of the volume rate is automatically displayed on the screen of the monitor 11 by the processor unit 39.

Furthermore, in the case of a scan condition that is not directly input by a user and cannot be calculated on the basis of other input scan conditions, a predetermined value is automatically input. In addition, the processor unit 39 may urge a user to input a non-input scan condition in a positive way, for example, by displaying a button, which corresponds to the non-input scan condition, so as to be reversed on the screen of FIG. 2. Moreover, in the case when other scan conditions cannot be set (that is, correlated scan conditions are not compatible) if some of the input scan conditions are adopted, the processor unit 39 displays that input values of the scan conditions and the like are errors on the screen of the monitor 11.

[Function for Adjusting a Sectional Position]

The function for adjusting a sectional position enables an arbitrary section, which is set for volume data obtained by three-dimensional trigger scan, to be set and changed to an arbitrary value or position in a stage before a three-dimensional trigger scan mode. In the three-dimensional trigger scan mode, an image related to the set and changed section of the acquired volume data is displayed.

Figure 4:
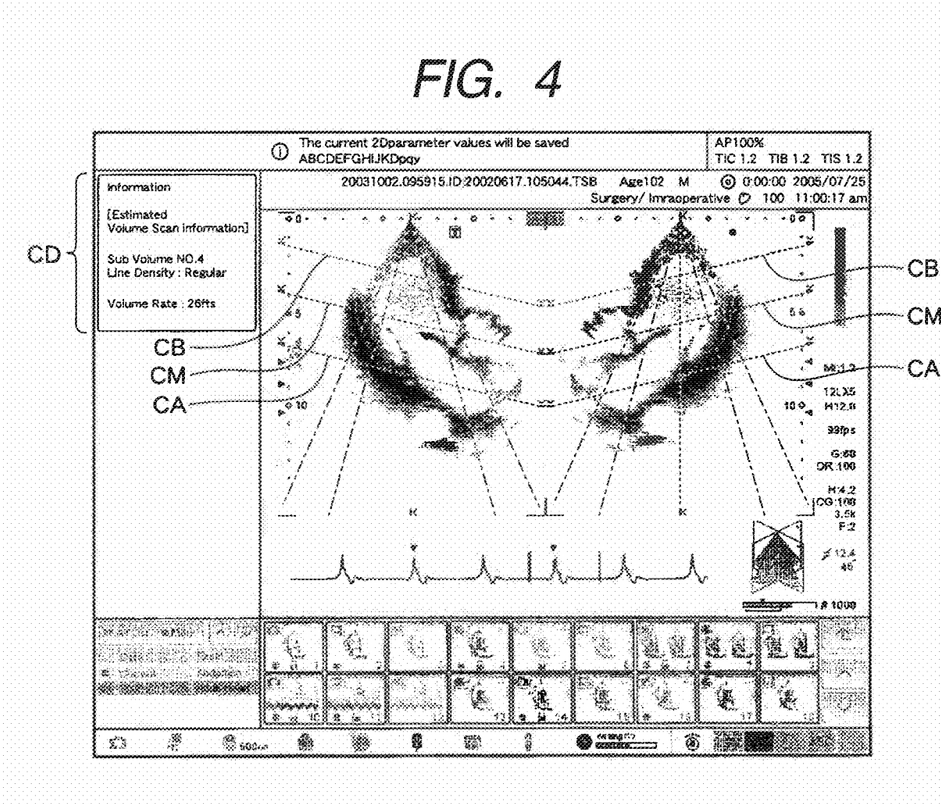
FIG. 4 is a view explaining a function for adjusting the sectional position by the processor unit shown in FIG. 1 and illustrates an example of a screen on which a Basal plane, a Mid plane, and an Apical plane set in a bi-plane image acquired by prescan are displayed.

FIG. 4 is a view explaining a function for adjusting the sectional position. FIG. 4 shows an example of a screen of the monitor 11 that displays a Basal plane CB, a Mid plane CM, and an Apical plane CP set for the bi-plane image BP acquired by prescan.

For example, positions of the Basal plane CB, the Mid plane CM, and the Apical plane CP may be set and changed when a 'C Plane Shift' is selected on the screen shown in FIG. 2. In this state, for example, when the positions of the Basal plane CB, the Mid plane CM, and the Apical plane CP shown on (either one of) the bi-plane image BP of FIG. 4 are adjusted (moved in parallel) by a mouse or an exclusive switch, for example, the processor unit 39 sets or changes each sectional position of volume data acquired by three-dimensional trigger scan to the respective positions of the Basal plane CB, the Mid plane CM, and the Apical plane CP after adjustment.

In addition, for example, slopes of the Basal plane CB, the Mid plane CM, and the Apical plane CP may be set and changed when a 'C Plane Rotation (A)' is selected on the screen shown in FIG. 2. In this state, for example, when the slopes of the Basal plane CB, the Mid plane CM, and the Apical plane CP shown on the bi-plane image BP of FIG. 4 are adjusted by a mouse or an exclusive switch, for example, the processor unit 39 sets or changes the Basal plane CB, the Mid plane CM, and the Apical plane CP for the volume data acquired by three-dimensional trigger scan so as to correspond to the slopes of the Basal plane CB, the Mid plane CM, and the Apical plane CP after adjustment.

In addition, the adjustment of positions or slopes of the Basal plane CB, the Mid plane CM, and the Apical plane CP may be made in such a manner that the other planes are automatically adjusted when one plane is adjusted or each plane is adjusted individually.

Figure 5:
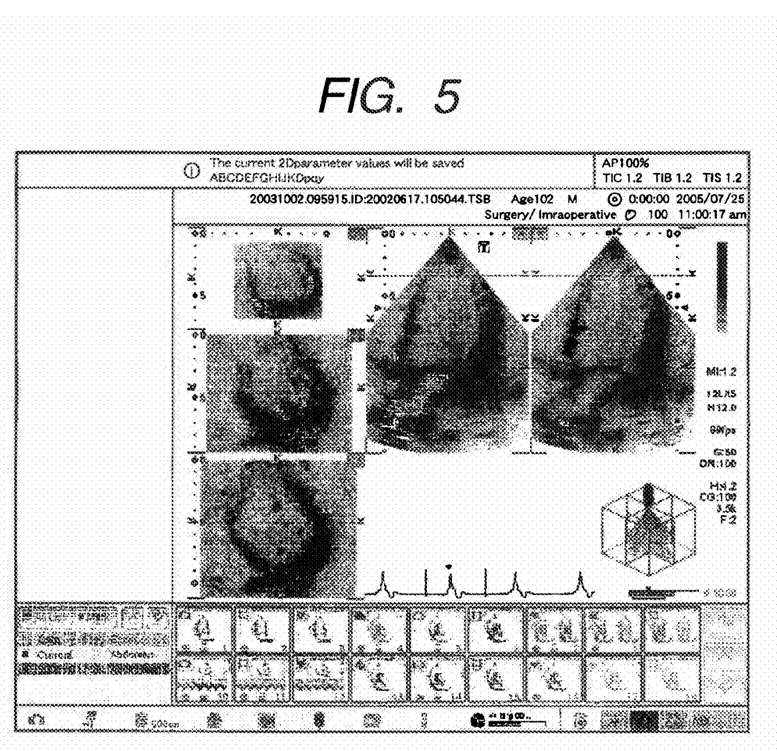
FIG. 5 is a view illustrating a bi-plane image and a C-mode image corresponding to each of the Basal plane, the Mid plane, and the Apical plane that are set by using a function for adjusting the sectional position by the processor unit shown in FIG. 1 and are automatically displayed in three-dimensional scan.

In this manner, when each of the Basal plane CB, the Mid plane CM, and the Apical plane CP is set to desired position and slope in a stage before three-dimensional trigger scan, the processor unit 39 sets each section, which corresponds to each of the set Basal plane CB, the Mid plane CM, and the Apical plane CP, on the volume data and generates a C-mode image and a bi-plane image corresponding to each plane at the time of the three-dimensional trigger scan. The C-mode image and the bi-plane image that are generated are automatically displayed in a form shown in FIG. 5, for example. Therefore, a user does not need to adjust the position and slope of each of the Basal plane CB, the Mid plane CM, and the Apical plane CP at the time of three-dimensional trigger scan.

[Function for Visualizing a Scan Range]

The function for visualizing a scan range enables a scan range in a three-dimensional trigger scan mode to be viewed in a stage before a three-dimensional trigger scan mode.

Figure 6:
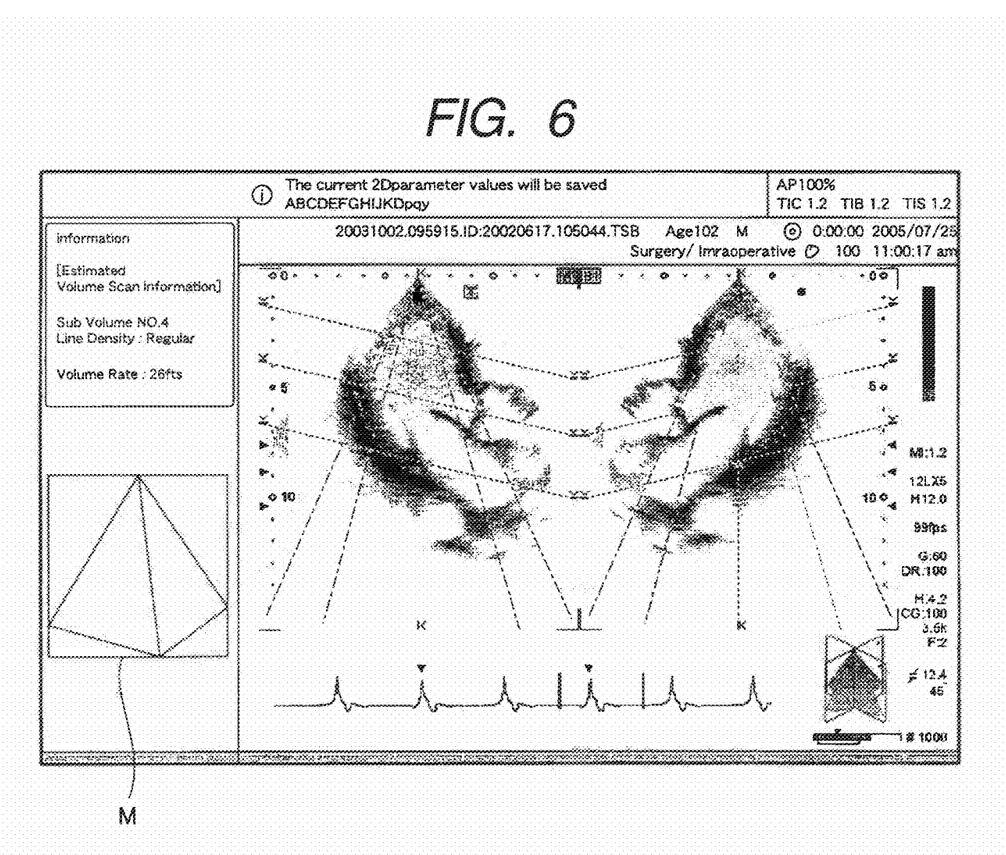
FIG. 6 is a view explaining a function for visualizing a scan range by the processor unit shown in FIG. 1 and illustrates an example of a screen on which a model schematically expressing a scan range in a three-dimensional trigger scan mode is displayed on the screen shown in FIG. 4.

FIG. 6 is a view explaining a function for visualizing a scan range. FIG. 6 shows an example of a model M of a scan range where a scan range in a three-dimensional trigger scan mode is schematically expressed on the screen shown in FIG. 4. The processor unit 39 generates the model M corresponding to the set scan range on the basis of the scan range, which is set and changed by using the function for simulating initial setting or scan conditions, and displays the generated model M on the screen of the monitor 11.

The processor unit 39 matches the spatial positions of the Model M and the bi-plane image BP on the basis of matching between the position on the screen and the position on a memory. Accordingly, for example, when the model M on the screen is rotated by the input device 13, the processor unit 39 rotates the bi-plane image BP in conjunction with the rotation. In addition, in the case when the bi-plane image BP is rotated due to rotation of the probe A caused by a checking doctor, for example, the processor unit 39 causes the scan range model M to rotate in a predetermined direction in conjunction with the rotation.

In addition, the display of the Model M is not limited to the above example. For example, the processor unit 39 may change a color and a pattern of the Model M according to a value of a frame rate.

[Function for Simulated Three-Dimensional Scan]

The function for simulated three-dimensional scan is a function of performing simulated three-dimensional scan on the basis of various kinds of scan conditions set by using the function for simulating a scan condition. The function for simulated three-dimensional scan is performed to simulate scan conditions, which are set by using the function for simulating a scan condition, mainly regarding three-dimensional scan. Any kind of three-dimensional scan can be performed as the simulated three-dimensional scan as long as various kinds of scan conditions set by using the function for simulating a scan condition are used in the three-dimensional scan. For example, the simulated three-dimensional scan is bi-plane scan in which scanning lines or frames are thinned out. In addition, since the prescan is not simulated three-dimensional scan but normal two-dimensional scan, it is possible to obtain an image having a high scan line density compared with an image obtained by the simulated three-dimensional scan. In addition, scan in a region excluding a three-dimensional scan range may be performed in high-density scan at the time of two-dimensional scan. Moreover, for a frame rate, a frame rate at the time of three-dimensional scan may not be simulated. In addition, data obtained by the simulated three-dimensional scan may be interpolated by signal processing or the like.

Figure 7:
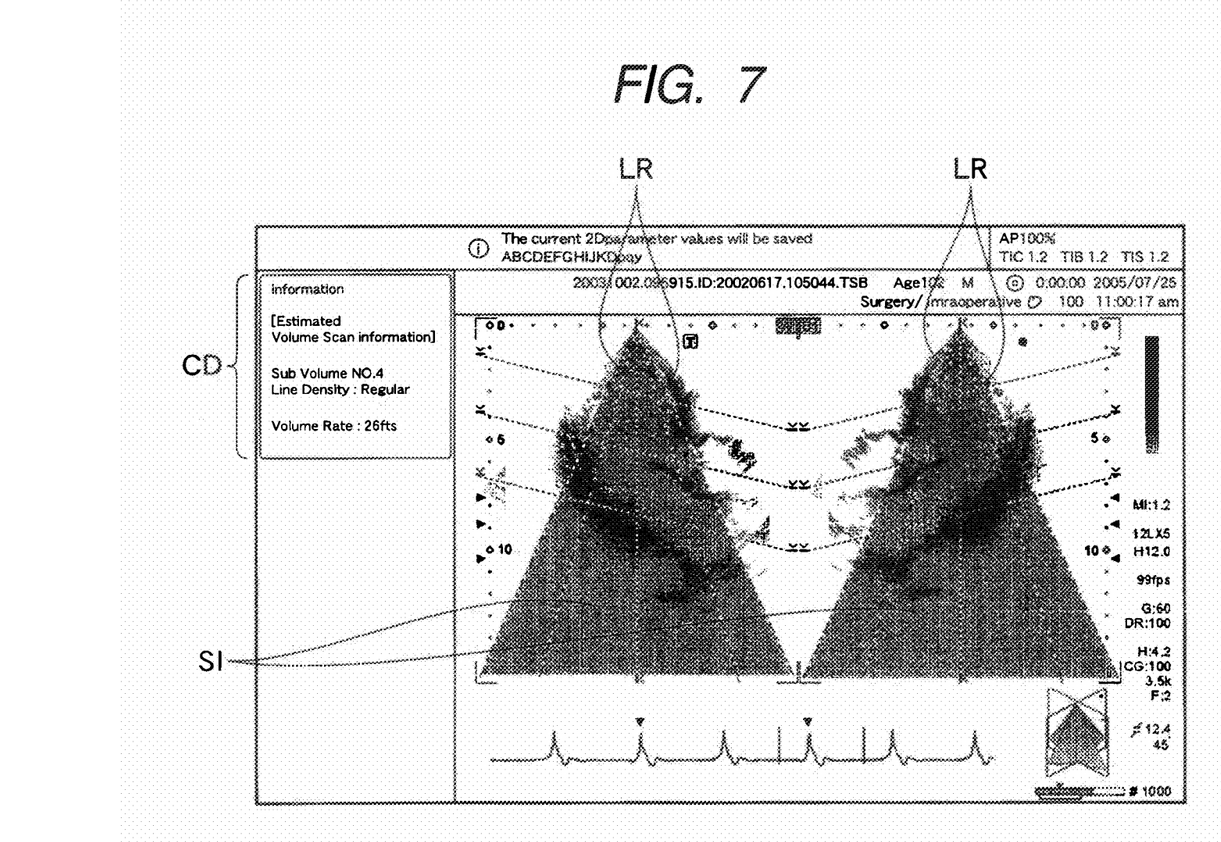
FIG. 7 is a view illustrating an example of an image that is acquired by simulated trigger scan and is displayed in a scan range set by using a function for simulating a scan condition by the processor unit shown in FIG. 1.

An image SI acquired by the simulated three-dimensional scan is displayed in a predetermined form within a scan range set by using the function for simulating a scan condition, as shown in FIG. 7. A user can quickly and easily guess an image, which is obtained by three-dimensional trigger scan, in a stage before a three-dimensional trigger scan by observing the displayed image.

(Operation)

Next, an operation of the ultrasonic diagnostic apparatus 1 in a three-dimensional trigger scan mode including processing for supporting three-dimensional trigger scan will be described.

Figure 8:
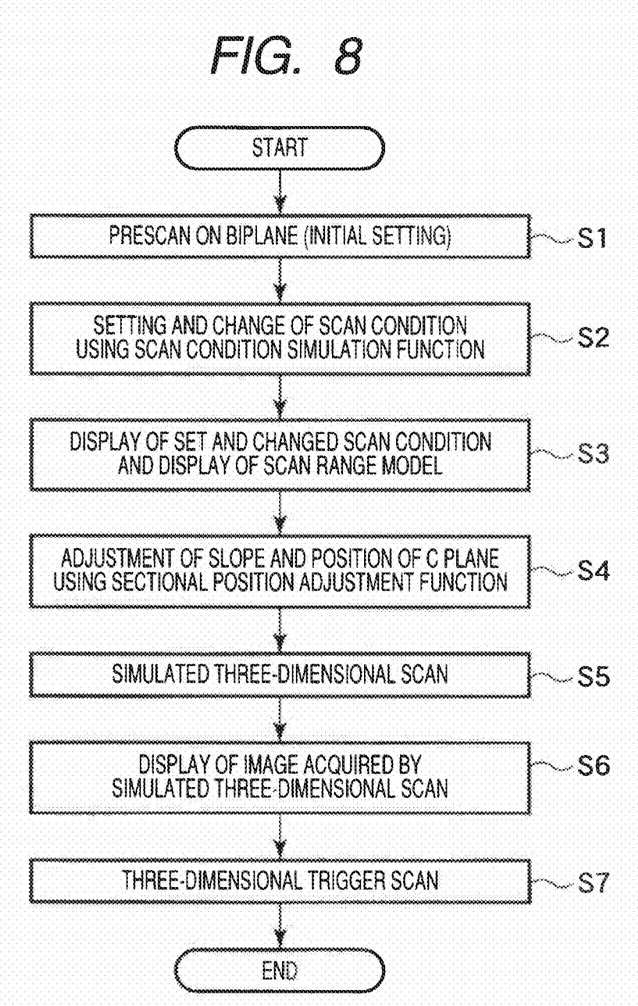
FIG. 8 is a flow chart illustrating each processing of a three-dimensional trigger scan mode performed under the control of the processor unit shown in FIG. 1.

FIG. 8 is a flow chart illustrating the flow of processing executed in a three-dimensional trigger scan mode. As shown in FIG. 8, the processor unit 39 first executes prescan on bi-plane using initial setting in the stage before the three-dimensional trigger scan mode (step S1).

Then, scan conditions are set and changed by using the function for simulating a scan condition described above (step S2). The processor unit 39 displays various kinds of set scan conditions and a model expressing the set scan range on the monitor 11 (step S3).

Then, the position and slope of the C surface is adjusted by using the function for adjusting a sectional position described above (step S4). Then, simulated three-dimensional scan using the various kinds of set scan conditions is executed (step S5). An image acquired by the simulated three-dimensional scan is displayed in a predetermined form on the screen of the monitor 11 (step S6).

In the case of modifying the various kinds of scan conditions, the C surface position, and the like set as described above, processing in steps S1 to step S6 is repeated. On the other hand, when the various kinds of scan conditions, the C surface position, and the like set as described above are not modified, three-dimensional trigger scan is executed by using the scan conditions. When the three-dimensional trigger scan is executed, a C-mode image and a bi-plane image corresponding to each set C surface are displayed, for example, in a layout shown in FIG. 5 (step S7).

(Effects)

According to the configuration described above, the following effects can be obtained.

According to the ultrasonic diagnostic apparatus 1, it is possible to simulate various kinds of scan conditions in a stage before three-dimensional trigger scan by using the function for simulating a scan condition. It is also possible to change a desired scan condition according to a result of the simulation. Accordingly, since all scan conditions can be checked in the stage before the three-dimensional trigger scan, it is possible to alleviate the work load of a user in the three-dimensional trigger scan.

Furthermore, according to the ultrasonic diagnostic apparatus 1, a section for observing volume data obtained by three-dimensional trigger scan can be set and changed to arbitrary position or slope using the function for adjusting a sectional position in a stage before the three-dimensional trigger scan. Accordingly, since it is not necessary to adjust the position of a C-mode image and the like in a stage of three-dimensional trigger scan, it is possible to alleviate the work load of a user in the three-dimensional trigger scan.

Furthermore, according to the ultrasonic diagnostic apparatus 1, a scan range in a three-dimensional trigger scan mode can be viewed in a stage before three-dimensional trigger scan by using the function for visualizing a scan range. Accordingly, it is not necessary to adjust the scan range in the actual stage of three-dimensional trigger scan. As a result, it is possible to alleviate the work load of a user in the three-dimensional trigger scan.

Furthermore, according to the ultrasonic diagnostic apparatus 1, it is possible to view an image obtained by simulating an image that is collected by actual three-dimensional trigger scan in a stage before the three-dimensional trigger scan by using the simulated three-dimensional scan. Therefore, it is possible to quickly and easily predict an image obtained by three-dimensional trigger scan and to prevent photographing from being repeatedly performed, for example. As a result, work loads of a user and a patient in the three-dimensional trigger scan can be reduced.

In addition, the invention is not limited to the embodiment described above but may be embodied in practice by modifying constituent components without departing from the scope and spirit of the invention. For example, specific modifications include the following examples.

FIRST MODIFIED EXAMPLE

In the present embodiment, three-dimensional trigger scan that particularly gives a heavy work load to a user in a scan preparation stage or at the time of scan has been described as an example of three-dimensional scan. However, in the present embodiment, the three-dimensional scan does not need to be limited to the three-dimensional trigger scan but may be utilized in all kinds of three-dimensional scanning methods. For example, a method of three-dimensional scan in the present embodiment may be a method of acquiring volume data on a desired three-dimensional region by performing typical three-dimensional scan, that is, performing direct three-dimensional scan for the entire three-dimensional region (that is, scanning the desired three-dimensional region without dividing desired three-dimensional region into a plurality of sub regions). The volume rate in the typical three-dimensional scan is calculated on the basis of at least the density of scan lines and a scan range by using the above-described function for simulating a scan condition by the processor unit 39.

SECOND MODIFIED EXAMPLE

In addition, the configuration of an apparatus body B is not limited to the configuration shown in FIG. 1. For example, the apparatus body in a second modified example includes a transmission unit 21, a receiving unit 23, a B-mode processing unit 25, a Doppler processing unit 27, and an image processing unit with a control unit as a main unit. The control unit is hardware including a processor unit (CPU) 39, a third memory, and a storage unit 37. The processor unit 39 reads a program for realizing a three-dimensional trigger scan function or an operating system for executing a predetermined scan sequence and image generation and display from the storage unit 37, loads the read programs onto the third memory, and executes various kinds of processing, operations, and controls. The third memory stores raw data generated in the B-mode processing unit 25 or the Doppler processing unit 27 for every scan line, every scan section, every scan volume, and every time-series volume data. In addition, the control unit connects sub volume data on the basis of trigger information, positional information, time-series information, and the like to thereby generate volume data in a desired range. Such connection processing may be performed in a stage of RAW data, or volume data after voxel conversion processing to be described later may be used.

The image processing unit is hardware including, for example, a GPU (graphics processing unit) that performs two-dimensional image processing or three-dimensional image processing. The image processing unit generates various kinds of volume data or images according to the above-described embodiment on the basis of data generated in the B-mode processing unit 25 or the Doppler processing unit 27 and data stored in the memory. For example, in the three-dimensional trigger scan mode, the image processing unit performs the voxel conversion processing on the RAW data, which is stored in the control unit, in high speed by using a parallel operation function of the GPU. In addition, the image processing unit generates an image related to the B plane or a C plane on the basis of the generated volume data in the desired range.

According to such a configuration, since each function can be realized as information processing using a CPU or a GPU, it is possible to use highly versatile hardware capable of performing high-speed processing. Since general-purpose hardware is used, the apparatus body of the second modified example can be manufactured at low cost.

In addition, various kinds of inventions may be realized by proper combination of the plurality of constituent components disclosed in the embodiment described above. For example, some constituent components may be eliminated from all components shown in the above embodiment. Moreover, constituent components in different embodiments may be appropriately combined.

Thus, according to the present embodiment, it becomes possible to provide an ultrasonic diagnostic apparatus and a control method thereof that can alleviate the work load of a user in a case of performing image collection in a three-dimensional scan mode compared with those in the related art.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   an ultrasonic probe;
   input circuitry implementing an input unit and configured to set or change a scan range, a density of scan lines, and a sub-volume number, wherein the scan range, the density of scan lines, and the sub-volume number are correlated to scan conditions for a three-dimensional trigger scan;
   a display configured to display at least one of the set or changed scan range, density of scan lines, and sub-volume number; and
   processing circuitry implementing an image acquisition unit, wherein the processing circuitry is configured to perform the three-dimensional trigger scan to generate volume data according to the set or changed scan range, density of scan lines, and sub-volume number by:
   controlling the ultrasonic probe to perform a three-dimensional scan for a plurality of sub-volumes constituting a three-dimensional region;
   generating a plurality of sub-volume data items corresponding to a predetermined range from raw data obtained from the three-dimensional scan; and
   connecting the acquired sub-volume data items based on a predetermined trigger to generate the volume data regarding the three-dimensional region according to the set or changed scan range, density of scan lines, and sub-volume number, wherein
   the processing circuitry further implements the image acquisition unit by being configured to acquire a prescan image regarding at least one section crossing the three-dimensional region by controlling the ultrasonic probe to perform a prescan in a stage before the three-dimensional trigger scan, the prescan being a scan other than the three-dimensional trigger scan,
   the display is further configured to display the acquired prescan image, and
   the input circuitry further implements the input unit by being configured to set or change the scan range and the sub-volume number on the displayed prescan image, wherein the set or changed sub-volume number is indicated as a total number of sub-volumes included in the displayed prescan image.

2. The ultrasonic diagnostic apparatus according to claim 1, wherein the display is further configured to display at least one of a determined volume rate, the set or changed scan range, the set or changed density of scan lines, together with the prescan image.

3. The ultrasonic diagnostic apparatus according to claim 1, wherein the processing circuitry further implements the image acquisition unit by being configured to acquire a bi-plane image as the prescan image.

4. The ultrasonic diagnostic apparatus according to claim 1,
   wherein the processing circuitry further implements a section setting unit and is configured to set at least one section on the prescan image, and
   wherein the display is configured to display a position of at least one set section on the prescan image.

5. The ultrasonic diagnostic apparatus according to claim 4,
   wherein the processing circuitry further implements the section setting unit by being configured to set a plane, which is not parallel to transmission and reception directions of ultrasonic waves, as at least one section.

6. The ultrasonic diagnostic apparatus according to claim 4, wherein
   the processing circuitry further implements the image acquisition unit by being configured to acquire a sectional image regarding at least one set section by the three-dimensional trigger scan, and
   the display is configured to display at least one acquired sectional image.

7. The ultrasonic diagnostic apparatus according to claim 4, wherein
   the processing circuitry further implements a changing unit and is configured to change at least one of position and slope of the section on the prescan image,
   the processing circuitry further implements the image acquisition unit by being configured to acquire a sectional image after the change regarding the section by the three-dimensional trigger scan, and
   the display is configured to display the acquired sectional image after the change.

8. The ultrasonic diagnostic apparatus according to claim 1,
wherein the display is configured to display a model, which schematically expresses the scan range, together with the prescan image.

9. The ultrasonic diagnostic apparatus according to claim 8,
wherein the processing circuitry further implements a matching unit and is configured to match spatial positions of the model and the prescan image, and
wherein the display is configured to move the prescan image in conjunction with the model on a basis of the spatial positions matching when an instruction of movement of the model has been made.

10. The ultrasonic diagnostic apparatus according to claim 1,
wherein the processing circuitry further implements the image acquisition unit by being configured to acquire the prescan image in order to simulate the set or changed scan range, density of scan lines, and sub-volume number and a determined volume rate.

11. The ultrasonic diagnostic apparatus according to claim 1,
wherein the processing circuitry further implements the image acquisition unit by being configured to acquire the prescan image by performing the prescan on a basis of the set or changed scan range, density of scan lines, and sub-volume number and a determined volume rate.

12. The ultrasonic diagnostic apparatus according to claim 1,
wherein the processing circuitry further implements a determination unit and is configured to determine a volume rate on a basis of the set or changed scan range, density of scan lines, and sub-volume number, and
wherein the processing circuitry further performs the three-dimensional trigger scan according to the set or changed scan range, density of scan lines, and sub-volume number and the determined volume rate.

13. A control method of an ultrasonic diagnostic apparatus, the control method comprising:
setting or changing a scan range, a density of scan lines, and a sub-volume number, wherein the scan range, the density of scan lines, and the sub-volume number are correlated scan conditions for three-dimensional trigger scan;
displaying at least one of the set or changed scan range, density of scan lines, and sub-volume number;
performing the three-dimensional trigger scan, using processing circuitry, according to the set or changed scan range, density of scan lines, and sub-volume number to generate volume data, the performing of the three-dimensional trigger scan comprising of controlling an ultrasonic probe to perform a three-dimensional scan for a plurality of sub-volumes constituting a three-dimensional region, generating a plurality of sub-volume data items corresponding to a predetermined range from raw data obtained from the three-dimensional scan, and connecting the acquired sub-volume data items based on a predetermined trigger to generate the volume data regarding the three-dimensional region according to the set or changed scan range, density of scan lines, and sub-volume number;
wherein the method further comprises:
acquiring a prescan image regarding at least one section crossing the three-dimensional region by performing a prescan using the ultrasonic probe in a stage before the three-dimensional trigger scan, the prescan being a scan other than the three-dimensional trigger scan;
displaying the acquired prescan image; and
setting or changing the sub-volume number on the displayed prescan image, wherein the set or changed sub-volume number is indicated as a total number of sub-volumes included in the displayed prescan image.

* * * * *